United States Patent
McGowan et al.

(10) Patent No.: US 11,076,765 B2
(45) Date of Patent: Aug. 3, 2021

(54) FFR SENSOR HEAD DESIGN THAT MINIMIZES STRESS INDUCED PRESSURE OFFSETS

(71) Applicant: BOSTON SCIENTIFIC SCIMED, INC., Maple Grove, MN (US)

(72) Inventors: Roger W. McGowan, Otsego, MN (US); Gregory Lee, Eden Prairie, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1393 days.

(21) Appl. No.: 14/341,374

(22) Filed: Jul. 25, 2014

(65) Prior Publication Data

US 2015/0032011 A1    Jan. 29, 2015

Related U.S. Application Data

(60) Provisional application No. 61/858,982, filed on Jul. 26, 2013.

(51) Int. Cl.
*A61B 5/0215* (2006.01)
*G01L 11/02* (2006.01)

(52) U.S. Cl.
CPC ........ *A61B 5/02154* (2013.01); *A61B 5/0215* (2013.01); *G01L 11/025* (2013.01)

(58) Field of Classification Search
CPC .................................................. A61B 5/0215
USPC ....................................................... 600/486
See application file for complete search history.

(56) References Cited

U.S. PATENT DOCUMENTS

| | | | |
|---|---|---|---|
| 3,273,447 A * | 9/1966 | Frank ................. | A61B 5/02154 359/846 |
| 3,963,323 A | 6/1976 | Arnold | |
| 4,771,782 A | 9/1988 | Millar | |
| 4,953,553 A | 9/1990 | Tremulis | |
| 4,983,824 A * | 1/1991 | Saaski .................... | G01D 5/266 250/227.23 |
| 5,106,455 A | 4/1992 | Jacobsen et al. | |

(Continued)

FOREIGN PATENT DOCUMENTS

| | | |
|---|---|---|
| DE | 202014100938 U1 | 3/2014 |
| EP | 0235992 A1 | 9/1987 |

(Continued)

*Primary Examiner* — Christian Jang
*Assistant Examiner* — Mitchell E Alter
(74) *Attorney, Agent, or Firm* — Seager, Tufte & Wickhem, LLP

(57) ABSTRACT

A pressure sensing medical device may include a guidewire including a tubular member having a lumen, the tubular member being translatable between a generally straightened position and a deflected position, and a pressure sensor attached at a distal end of a fiber optic extending within the lumen, the pressure sensor being disposed within a distal portion of the tubular member. The pressure sensor may include a pressure-sensitive membrane disposed on a distal end thereof. The pressure sensor may include one or more contact members capable of providing a contact point between the contact member and an inner surface of the tubular member when in the deflected position, the contact point being axially spaced apart from the membrane along a longitudinal axis of the pressure sensor.

20 Claims, 12 Drawing Sheets

(56) References Cited

U.S. PATENT DOCUMENTS

| | | | |
|---|---|---|---|
| 5,178,159 A | 1/1993 | Christian | |
| 5,238,004 A | 8/1993 | Sahatjian et al. | |
| 5,280,786 A * | 1/1994 | Wlodarczyk | A61B 5/1459 |
| | | | 356/41 |
| 5,313,957 A | 5/1994 | Little | |
| 5,421,195 A | 6/1995 | Wlodarczyk | |
| 5,422,969 A | 6/1995 | Eno | |
| 5,425,371 A * | 6/1995 | Mischenko | A61B 5/02154 |
| | | | 600/480 |
| 5,427,114 A | 6/1995 | Colliver et al. | |
| 5,438,873 A | 8/1995 | Wlodarczyk et al. | |
| 5,573,520 A | 11/1996 | Schwartz et al. | |
| 5,633,963 A | 5/1997 | Rickenbach et al. | |
| 5,755,668 A | 5/1998 | Itoigawa et al. | |
| 5,772,609 A | 6/1998 | Nguyen et al. | |
| 5,797,856 A | 8/1998 | Frisbie et al. | |
| 5,872,879 A | 2/1999 | Hamm | |
| 5,902,248 A | 5/1999 | Millar et al. | |
| 5,938,624 A | 8/1999 | Akerfeldt et al. | |
| 5,949,929 A | 9/1999 | Hamm | |
| 6,112,598 A | 9/2000 | Tenerz et al. | |
| 6,120,457 A | 9/2000 | Coombes et al. | |
| 6,139,510 A | 10/2000 | Palmero | |
| 6,162,182 A | 12/2000 | Cole | |
| 6,167,763 B1 | 1/2001 | Tenerz et al. | |
| 6,196,980 B1 | 3/2001 | Akerfeldt et al. | |
| 6,248,083 B1 | 6/2001 | Smith et al. | |
| 6,265,792 B1 | 7/2001 | Granchukoff | |
| 6,394,986 B1 | 5/2002 | Millar | |
| 6,398,738 B1 | 6/2002 | Millar | |
| 6,409,677 B1 | 6/2002 | Tulkki | |
| 6,428,336 B1 | 8/2002 | Akerfeldt | |
| 6,508,803 B1 | 1/2003 | Horikawa et al. | |
| 6,565,514 B2 | 5/2003 | Svanerudh et al. | |
| 6,579,246 B2 | 6/2003 | Jacobsen et al. | |
| 6,585,660 B2 | 7/2003 | Dorando et al. | |
| 6,615,067 B2 | 9/2003 | Hoek et al. | |
| 6,663,570 B2 | 12/2003 | Mott et al. | |
| 6,766,720 B1 | 7/2004 | Jacobsen et al. | |
| 6,767,327 B1 | 7/2004 | Corl et al. | |
| 6,776,720 B2 | 8/2004 | Bartlett | |
| 6,908,442 B2 | 6/2005 | Von Malmborg et al. | |
| 6,918,882 B2 | 6/2005 | Skujins et al. | |
| 6,918,873 B1 | 7/2005 | Millar et al. | |
| 6,974,422 B1 | 12/2005 | Millar | |
| 6,976,965 B2 | 12/2005 | Corl et al. | |
| 6,993,974 B2 | 2/2006 | Tenerz et al. | |
| 6,994,695 B1 | 2/2006 | Millar | |
| 7,071,197 B2 | 7/2006 | Leonardi et al. | |
| 7,134,994 B2 | 11/2006 | Alpert et al. | |
| 7,162,926 B1 | 1/2007 | Guziak et al. | |
| 7,187,453 B2 | 3/2007 | Belleville | |
| 7,259,862 B2 | 8/2007 | Duplain et al. | |
| 7,265,847 B2 | 9/2007 | Duplain et al. | |
| 7,274,956 B2 | 9/2007 | Mott et al. | |
| 7,331,236 B2 | 2/2008 | Smith et al. | |
| 7,532,920 B1 | 5/2009 | Ainsworth | |
| 7,618,379 B2 | 11/2009 | Reynolds et al. | |
| 7,684,657 B2 | 3/2010 | Donlagic et al. | |
| 7,689,071 B2 | 3/2010 | Belleville et al. | |
| 7,715,903 B2 | 5/2010 | Hartley et al. | |
| 7,724,148 B2 | 5/2010 | Samuelsson et al. | |
| 7,731,664 B1 | 6/2010 | Millar | |
| 7,759,633 B2 | 7/2010 | Duplain et al. | |
| 7,783,338 B2 | 8/2010 | Ainsworth et al. | |
| 7,878,984 B2 | 2/2011 | Davis et al. | |
| 7,930,014 B2 | 4/2011 | Huenneckens et al. | |
| 7,946,997 B2 | 5/2011 | Hübinette | |
| 8,025,623 B1 | 9/2011 | Millar | |
| 8,029,447 B2 | 10/2011 | Kanz et al. | |
| 8,174,395 B2 | 5/2012 | Samuelsson et al. | |
| 8,216,151 B2 | 7/2012 | Smith | |
| 8,298,156 B2 | 10/2012 | Manstrom et al. | |
| 8,317,715 B2 | 11/2012 | Belleville et al. | |
| 8,343,076 B2 | 1/2013 | Sela et al. | |
| 8,393,802 B2 | 3/2013 | Stanley et al. | |
| 8,410,940 B2 | 4/2013 | Samuelsson et al. | |
| 8,461,997 B2 | 6/2013 | Samuelsson et al. | |
| 8,485,985 B2 | 7/2013 | Manstrom et al. | |
| 8,555,712 B2 | 10/2013 | Narvaez et al. | |
| 8,556,820 B2 | 10/2013 | Alpert et al. | |
| 8,562,537 B2 | 10/2013 | Alpert et al. | |
| 8,583,218 B2 | 11/2013 | Eberle | |
| 8,636,659 B2 | 1/2014 | Alpert et al. | |
| 8,641,633 B2 | 2/2014 | Smith | |
| 8,641,639 B2 | 2/2014 | Manstrom et al. | |
| 8,676,299 B2 | 3/2014 | Schmitt et al. | |
| 8,698,638 B2 | 4/2014 | Samuelsson et al. | |
| 8,752,435 B2 | 6/2014 | Belleville et al. | |
| 8,936,401 B2 | 1/2015 | Belleville et al. | |
| 8,998,823 B2 | 4/2015 | Manstrom et al. | |
| 9,052,466 B2 | 6/2015 | Belleville et al. | |
| 2003/0069522 A1 | 4/2003 | Jacobsen et al. | |
| 2004/0073141 A1 | 4/2004 | Hartley et al. | |
| 2004/0181174 A2 | 9/2004 | Davis et al. | |
| 2005/0000294 A1 | 1/2005 | Tenerz et al. | |
| 2006/0122537 A1 | 6/2006 | Reynolds et al. | |
| 2006/0133715 A1 * | 6/2006 | Belleville | G01L 9/0079 |
| | | | 385/13 |
| 2008/0119758 A1 | 5/2008 | Samuelsson et al. | |
| 2009/0082678 A1 | 3/2009 | Smith | |
| 2009/0192412 A1 | 7/2009 | Sela et al. | |
| 2010/0145308 A1 | 6/2010 | Layman et al. | |
| 2010/0241008 A1 | 9/2010 | Belleville et al. | |
| 2011/0071407 A1 | 3/2011 | Hübinette et al. | |
| 2011/0178413 A1 | 7/2011 | Schmitt et al. | |
| 2011/0186294 A1 | 8/2011 | Narvaez et al. | |
| 2011/0319773 A1 | 12/2011 | Kanz et al. | |
| 2012/0227505 A1 * | 9/2012 | Belleville | G01L 9/0042 |
| | | | 73/705 |
| 2012/0265102 A1 | 10/2012 | Leo et al. | |
| 2013/0051731 A1 | 2/2013 | Belleville et al. | |
| 2013/0218032 A1 | 8/2013 | Belleville | |
| 2013/0296718 A1 | 11/2013 | Ranganathan et al. | |
| 2013/0317372 A1 | 11/2013 | Eberle et al. | |
| 2014/0005558 A1 | 1/2014 | Gregorich | |
| 2014/0058275 A1 | 2/2014 | Gregorich et al. | |
| 2014/0081244 A1 | 3/2014 | Voeller et al. | |
| 2014/0107624 A1 | 4/2014 | Belleville | |
| 2014/0121475 A1 | 5/2014 | Alpert et al. | |
| 2014/0168659 A1 * | 6/2014 | Suri | G01D 5/268 |
| | | | 356/480 |
| 2014/0180031 A1 * | 6/2014 | Anderson | A61B 8/0891 |
| | | | 600/301 |
| 2014/0241669 A1 | 8/2014 | Belleville et al. | |
| 2014/0248021 A1 | 9/2014 | Belleville et al. | |
| 2015/0301288 A1 | 10/2015 | Thornton, Jr. | |

FOREIGN PATENT DOCUMENTS

| | | | |
|---|---|---|---|
| EP | 0738495 A1 | 10/1996 | |
| EP | 0879615 A1 | 11/1998 | |
| EP | 0879617 A1 | 11/1998 | |
| EP | 1479407 A1 | 11/2004 | |
| JP | 2005291945 A | 10/2005 | |
| JP | 2014042645 A | 3/2014 | |
| WO | 9313707 A1 | 7/1993 | |
| WO | 9533983 A1 | 12/1995 | |
| WO | 9945352 A1 | 9/1999 | |
| WO | 2008034010 A2 | 3/2008 | |
| WO | 2011027282 A1 | 3/2011 | |
| WO | 2011090744 A2 | 7/2011 | |
| WO | 2011123689 A1 | 10/2011 | |
| WO | 2012000798 A1 | 1/2012 | |
| WO | 2012090210 A1 | 7/2012 | |
| WO | WO 2012009021 * | 7/2012 | G01D 5/268 |
| WO | 2013033489 A1 | 3/2013 | |
| WO | 2014025255 A1 | 2/2014 | |

* cited by examiner

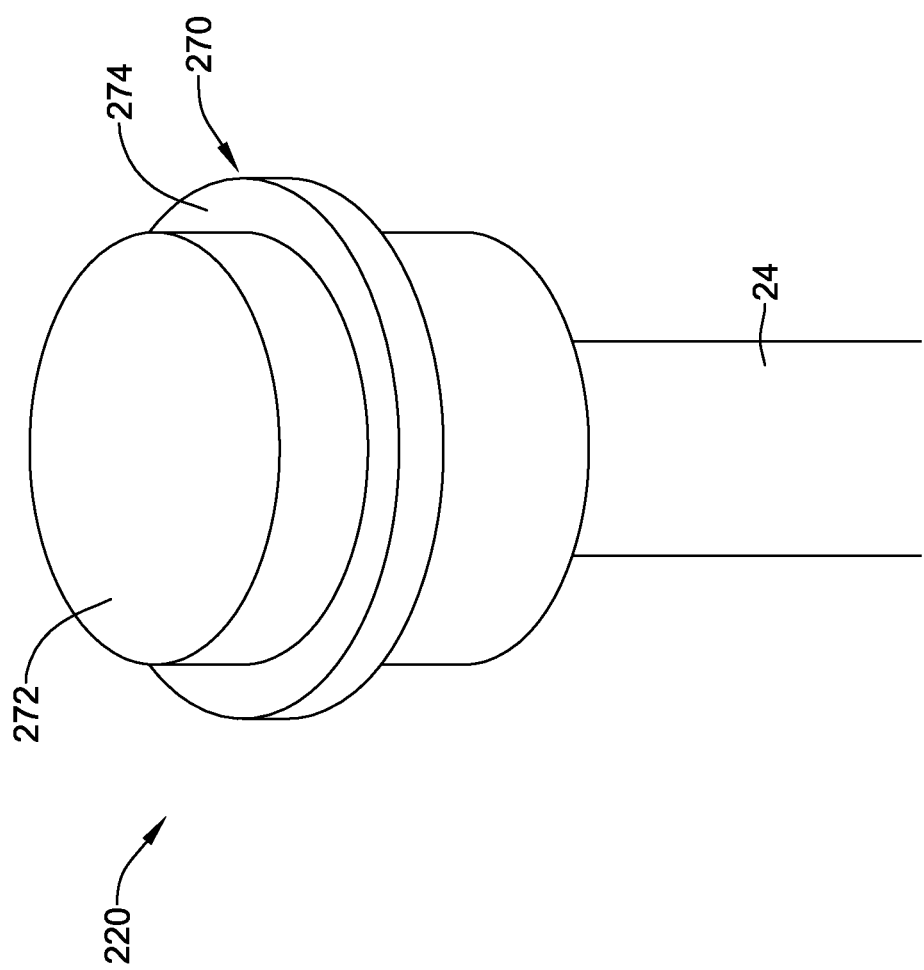

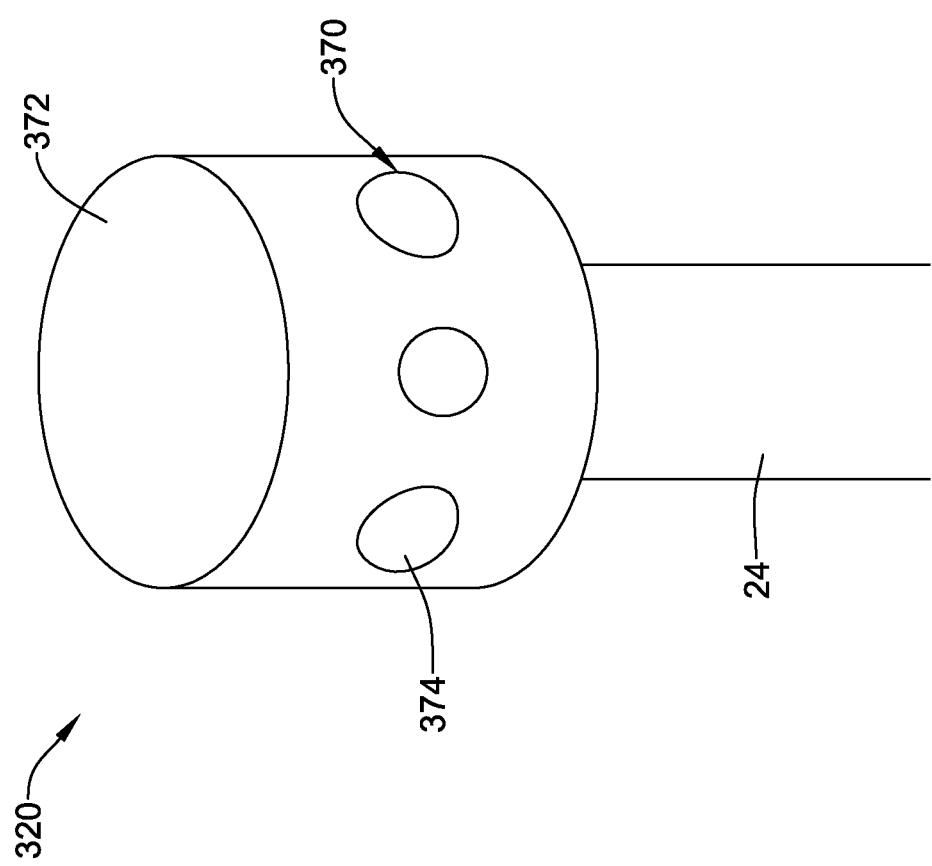

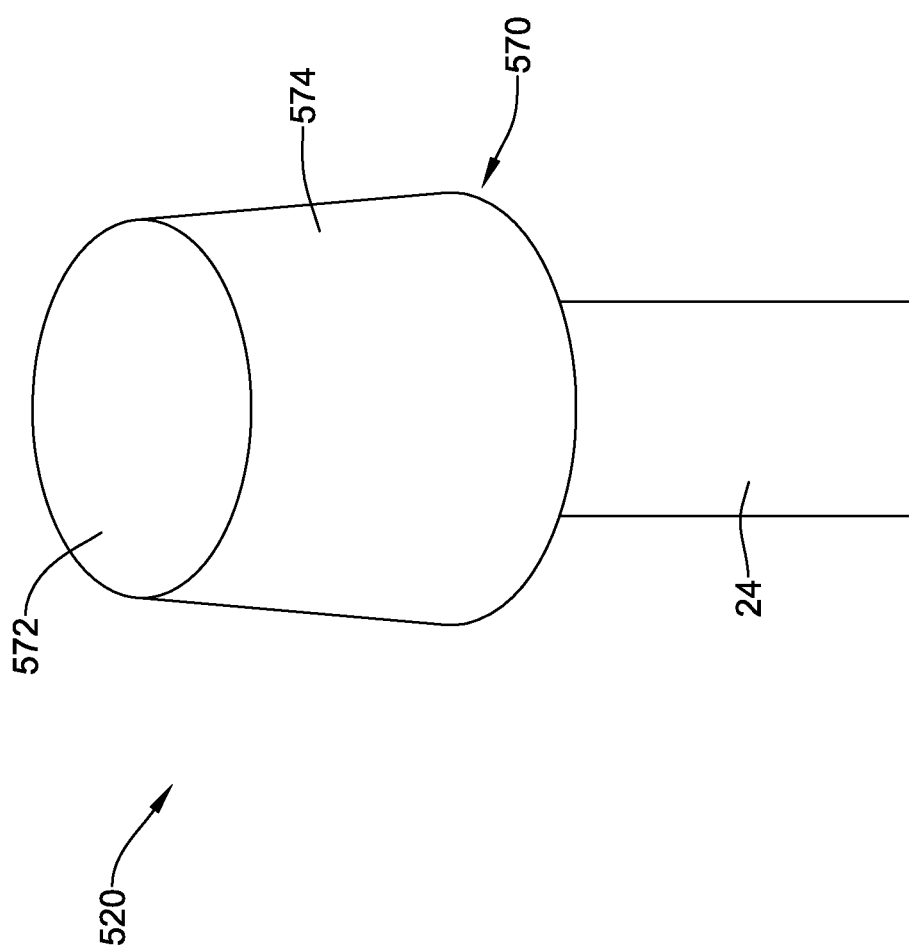

FFR SENSOR HEAD DESIGN THAT MINIMIZES STRESS INDUCED PRESSURE OFFSETS

CROSS-REFERENCE TO RELATED APPLICATIONS

This application claims priority under 35 U.S.C. § 119 to U.S. Provisional Application Ser. No. 61/858,982, filed Jul. 26, 2013, the entirety of which is incorporated herein by reference.

TECHNICAL FIELD

The present disclosure pertains to medical devices, and methods for manufacturing medical devices. More particularly, the present disclosure pertains to blood pressure sensing guidewires and methods for using pressure sensing guidewires.

BACKGROUND

A wide variety of intracorporal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

A pressure sensing medical device may include a guidewire including an elongate tubular member having a lumen extending therethrough, and an optical pressure sensor attached at a distal end of a fiber optic extending longitudinally within the lumen, the pressure sensor being disposed within a distal portion of the tubular member, wherein the pressure sensor further includes a contact member capable of providing a contact point between the contact member and an inner surface of the tubular member, the contact point being axially spaced apart from a distal end of the pressure sensor.

A pressure sensing medical device may include a guidewire including an elongate tubular member having a lumen extending therethrough, the tubular member being movable between a generally straightened position and a deflected position, and an optical pressure sensor attached at a distal end of a fiber optic extending longitudinally within the lumen, the pressure sensor being disposed within a distal portion of the tubular member, wherein the pressure sensor includes a pressure-sensitive membrane disposed on a distal end thereof, wherein the pressure sensor further includes one or more contact members capable of providing a contact point between the contact member and an inner surface of the tubular member when in the deflected position, the contact point being axially spaced apart from the membrane along a longitudinal axis of the pressure sensor.

A pressure sensing medical device may include a guidewire including an elongate tubular member having a lumen extending therethrough, the tubular member being movable between a generally straightened position and a deflected position, and an optical pressure sensor attached at a distal end of a fiber optic extending longitudinally within the lumen, the pressure sensor being disposed within a distal portion of the tubular member, wherein the pressure sensor includes a pressure-sensitive membrane disposed on a distal end thereof, wherein the pressure sensor further includes one or more contact members capable of providing a contact point between the contact member and an inner surface of the tubular member when in the deflected position such that the membrane is spaced apart from the inner surface, the contact point being axially spaced apart from the membrane along a longitudinal axis of the pressure sensor.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which:

FIG. 4 is a partial perspective view of an example sensor head;

FIG. 5 is a partial perspective view of an example sensor head;

FIG. 7 is a partial perspective view of an example sensor head; and

Figure 1:
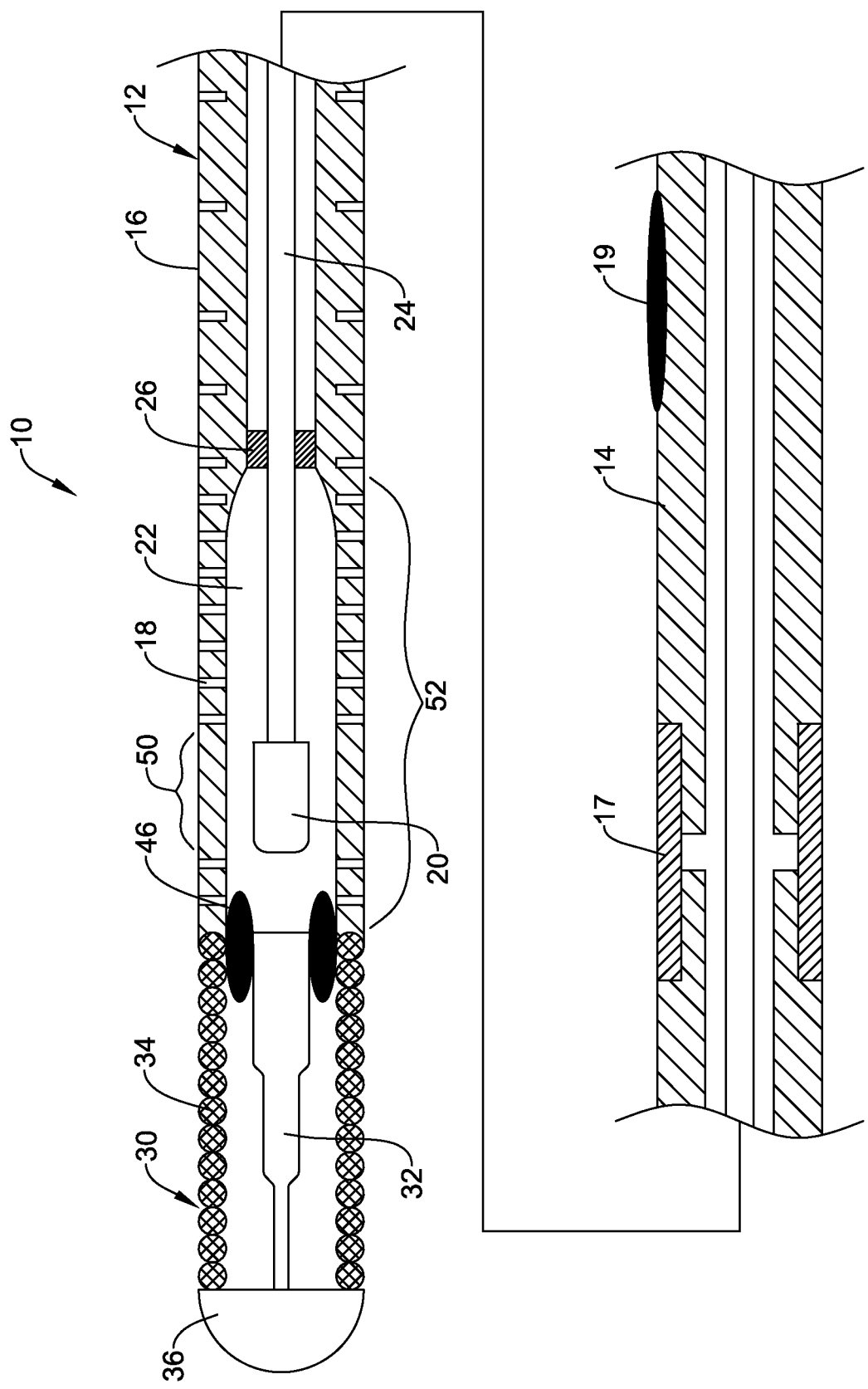
FIG. 1 is a partial cross-sectional side view of a portion of an example medical device in a generally straightened position.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

During some medical interventions, it may be desirable to measure and/or monitor the blood pressure within a blood vessel. For example, some medical devices may include pressure sensors that allow a clinician to monitor blood pressure. In some cases, such devices may be useful in determining fractional flow reserve (FFR), which may be understood as the pressure after or downstream from a stenosis relative to the pressure before or upstream from the stenosis. In some embodiments, the pressure sensor(s) may monitor aortic pressure. A number of pressure sensing devices, however, may pose technical challenges for maintaining accurate pressure measurements or readings when steering, tracking, torquing, or otherwise navigating the device within the vasculature or other suitable anatomy. Disclosed herein are medical devices that include pressure sensing capabilities and may be steered, tracked, torqued, and/or otherwise navigated through the anatomy while maintaining accurate pressure measurements or readings.

FIG. 1 illustrates a portion of an example medical device 10. In this example, a medical device 10 is a blood pressure sensing guidewire 10. However, this is not intended to be limiting as other medical devices are contemplated including, for example, catheters, shafts, leads, wires, or the like. The guidewire 10 may include a guidewire shaft or tubular member 12. Tubular member 12 may include a proximal portion 14 and a distal portion 16. The materials for the proximal portion 14 and the distal portion 16 may vary and may include those materials disclosed herein. For example, the distal portion 16 may include a nickel-cobalt-chromium-molybdenum alloy (e.g., MP35-N). The proximal portion 14 may include stainless steel. These are just examples. Other materials may also be utilized as discussed below.

In some embodiments, the proximal portion 14 and the distal portion 16 are formed from the same monolith of material. In other words, the proximal portion 14 and the distal portion 16 are portions of the same tube defining the tubular member 12. In other embodiments, the proximal portion 14 and the distal portion 16 are separate tubular members that are joined together. For example, a section of the outer surface of the proximal portion 14 and the distal portion 16 may be removed and a sleeve 17 may be disposed over the removed section(s) to join the proximal portion 14 and the distal portion 16. Alternatively, the sleeve 17 may be simply disposed over the proximal portion 14 and/or the distal portion 16. Other bonds may also be used including welds, thermal bonds, adhesive bonds, or the like. If utilized, the sleeve 17 used to join the proximal portion 14 with the distal portion 16 may include a material that desirably bonds with both the proximal portion 14 and the distal portion 16. For example, the sleeve 17 may include a nickel-chromium-molybdenum alloy (e.g., INCONEL), or other suitable material as discussed below.

A plurality of slots 18 may be formed in the tubular member 12. In at least some embodiments, the plurality of slots 18 is formed in the distal portion 16. In at least some embodiments, the proximal portion 14 lacks the plurality of slots 18. However, the proximal portion 14 may include the plurality of slots 18. The plurality of slots 18 may be desirable for a number of reasons. For example, the plurality of slots 18 may provide a desirable level of flexibility to the tubular member 12 (e.g., along the distal portion 16) while also allowing suitable transmission of torque. The plurality of slots 18 may be arranged/distributed along the distal portion 16 in a suitable manner including any of those arrangements disclosed herein. For example, the plurality of slots 18 may be arranged as opposing pairs of slots that are distributed along the length of the distal portion 16. In some embodiments, adjacent pairs of slots may have a substantially constant spacing relative to one another. Alternatively, the spacing between adjacent pairs of slots may vary. For example, more distal regions of the distal portion 16 may have a decreased spacing (and/or increased slot density), which may provide increased flexibility. In other embodiments, more distal regions of the distal portion 16 may have an increased spacing (and/or decreased slot density). These are just examples. Other arrangements are contemplated.

A pressure sensor 20 may be disposed within the distal portion 16 of the tubular member 12 (e.g., within a lumen 22 of the tubular member 12). While the pressure sensor 20 is shown schematically in FIG. 1, it may be appreciated that the structural form and/or type of the pressure sensor 20 may vary. For example, the pressure sensor 20 may include a semiconductor (e.g., silicon wafer) pressure sensor, piezoelectric pressure sensor, a fiber optic or optical pressure sensor, a Fabry-Perot type pressure sensor, an ultrasound transducer and/or ultrasound pressure sensor, a magnetic pressure sensor, a solid-state pressure sensor, or the like, or any other suitable pressure sensor.

As indicated above, the pressure sensor 20 may include an optical pressure sensor. In at least some of these embodiments, an optical fiber or fiber optic 24 may be attached to the pressure sensor 20 and may extend longitudinally within the lumen 22. At least one attachment member 26 may fixedly attach the fiber optic 24 to the tubular member 12 within, at, or near the distal portion 16. The at least one attachment member 26 may be circumferentially disposed about and attached to the fiber optic 24 and may be secured to the inner surface of the tubular member 12 (e.g., the distal portion 16). In at least some embodiments, the at least one attachment member 26 may be proximally spaced apart from the pressure sensor 20. Other arrangements are contemplated.

In at least some embodiments, the distal portion 16 may include a region with a thinned wall and/or an increased inner diameter that defines a housing region 52. In general, the housing region 52 may be a region of the distal portion 16 that ultimately "houses" the pressure sensor 20. By virtue of having a portion of the inner wall of the tubular member 12 being removed at the housing region 52, additional space may be created or otherwise defined that can accommodate the pressure sensor 20.

In at least some embodiments, it may be desirable for the pressure sensor 20 to have reduced exposure along its side surfaces to fluid pressure (e.g., from the blood). Accordingly, it may be desirable to position the pressure sensor 20 along a landing region 50 defined along the housing region 52. The landing region 50 may be substantially free of slots so that the side surfaces of the pressure sensor 20 have a reduced likelihood of being deformed due to fluid pressures at these locations. Distal of the landing region 50, the housing region 52 may include slots or apertures that provide fluid access to the pressure sensor 20.

In some embodiments, the plurality of slots 18 may define a fluid pathway that allows blood (and/or a body fluid) to flow from a position along the exterior or outer surface of the guidewire 10 (and/or the tubular member 12), through the plurality of slots 18, and into the lumen 22 of the tubular member 12, where the blood can come into contact with the pressure sensor 20. Because of this, no additional side openings/holes (e.g., other than the plurality of slots 18) may be necessary in the tubular member 12 for pressure measurement. This may also allow the length of the distal portion 16 to be shorter than typical sensor mounts or hypotubes that would need to have a length sufficient for a suitable opening/hole (e.g., a suitable "large" opening/hole) to be formed therein that provides fluid access to the pressure sensor 20.

In at least some embodiments, a sealing member (not shown) may be disposed within the tubular member 12. The sealing member may be generally capable of sealing or otherwise preventing body fluids that enter the lumen 22 (e.g., through the plurality of slots 18) from passing through the tubular member 12 to the proximal portion 14 and/or out of the guidewire 10 at the proximal end. The sealing member may be positioned at a suitable location along the tubular member 12 proximal of the distal portion 14 and/or the pressure sensor 20. This may include being positioned proximal of the plurality of slots 18. While a single sealing member may be utilized, additional sealing members may also be utilized and the additional sealing members may be positioned at one or more suitable locations along the tubular member 12.

A tip member 30 may be coupled to the distal portion 16. The tip member 30 may include a shaping member 32 and a spring or coil member 34. A distal tip 36 may be attached to the shaping member 32 and/or the spring 34. In at least some embodiments, the distal tip 36 may take the form of a solder ball tip. The tip member 30 may be joined to the distal portion 16 of the tubular member 12 with a bonding member 46 such as a weld.

The tubular member 12 may include a hydrophilic coating 19. In some embodiments, the hydrophilic coating 19 may extend along substantially the full length of the tubular member 12. In other embodiments, one or more discrete sections of the tubular member 12 may include the hydrophilic coating 19.

In some embodiments, the proximal end of the guidewire 10 may be capable of attaching to a connector or handle member. The handle member may include a suitable connector for a cable to attach thereto and extend to another suitable device such as a signal conditioner or interferometer. Another cable may extend from the signal conditioner or interferometer to a suitable output device or display and/or monitoring unit. A clinician may utilize the readings from the output device to tailor the intervention to the needs of the patient or otherwise advance the goals of the intervention. These are just examples. Other devices and/or arrangements may be utilized with the guidewire 10.

In some embodiments, the pressure sensor 20, as discussed above, may include an optical pressure sensor. The pressure sensor 20 may generally include a head attached at a distal end of a fiber optic 24. The head of the pressure sensor 20 may include a pressure-sensitive membrane 72 on a distal end thereof. In some embodiments, the membrane 72 may extend across the distal end of the pressure sensor 20. In some embodiments, the membrane 72 may extend across a portion of the distal end of the pressure sensor 20. For example, in some embodiments, the membrane 72 may be substantially centered on the distal end of the pressure sensor 20, but may not extend or reach to or over an edge of the distal end of the pressure sensor 20. The membrane 72 may be very sensitive and may move, pulsate, vibrate, or otherwise translate proximally and distally in response to pressure exerted on it by the surrounding blood or fluid. Light transmitted through the head of the pressure sensor 20 from the fiber optic 24 may be reflected off the membrane 72. The reflected light may processed by an external processing unit, thereby "sensing" and consequently displaying the pressure of the surrounding blood or fluid.

Figure 2:
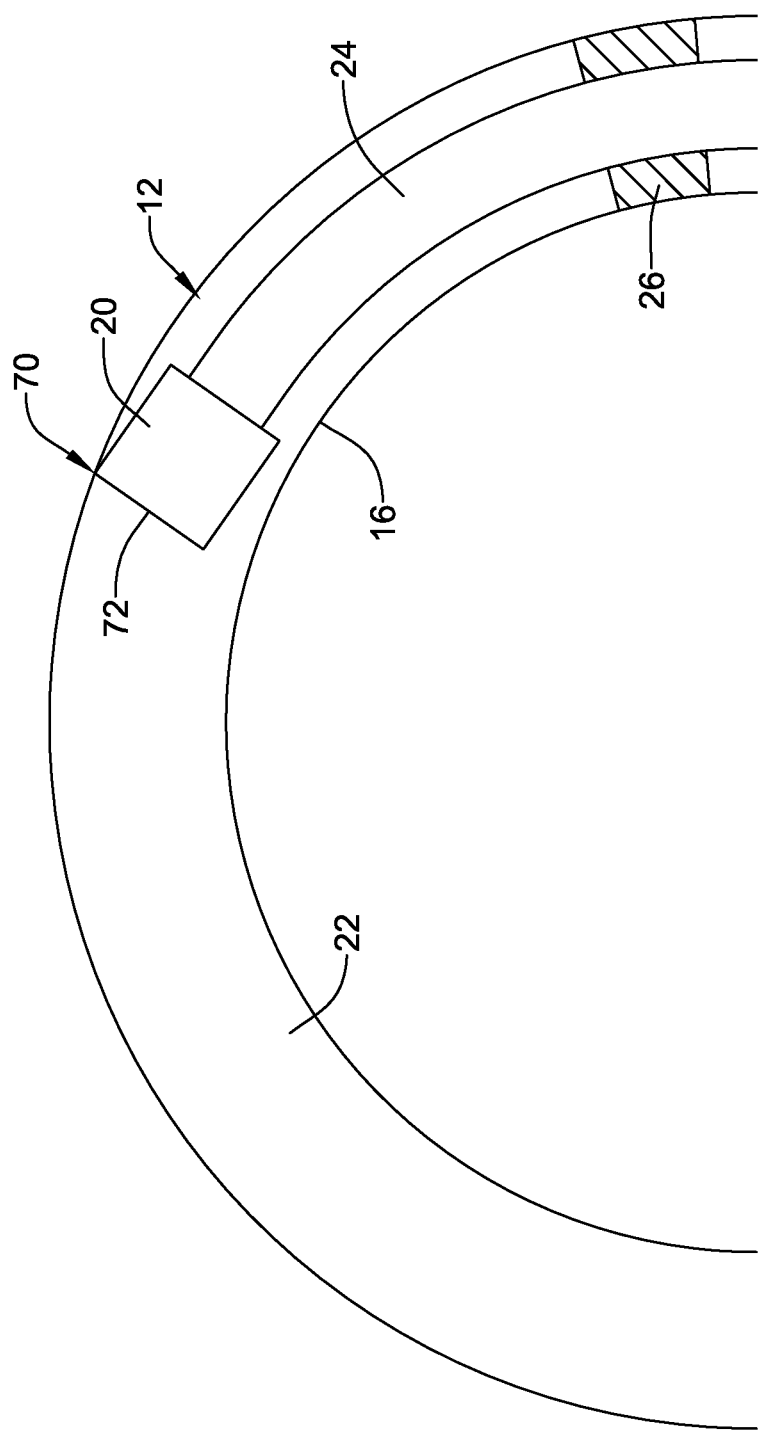
FIG. 2 is a partial cross-sectional side view of an example medical device in a deflected position.

In some embodiments, the guidewire 10 may be used in tortuous vasculature, which causes the guidewire 10 to be bent, curved, twisted, or otherwise distorted from a generally straightened position (i.e., straight or unstressed) as shown in FIG. 1, to a deflected position, as illustrated in FIG. 2 for example. In other words, the guidewire 10 may be translatable or movable between a generally straightened position and a deflected position.

In some embodiments, the head of the pressure sensor 20 may be suspended within the lumen 22 of the tubular member 12 distal of the at least one attachment member 26 by a portion of the fiber optic 24. A lever arm may be considered to be formed or defined by the portion of the fiber optic 24 distal of the at least one attachment member 26 and the pressure sensor 20. In other words, the lever arm may be defined as the distance from the at least one attachment member 26 to the distal end of the pressure sensor 20. Placement of the at least one attachment member 26 within the tubular member 12 may vary, and thereby increase or decrease a length of the lever arm.

In use, as the guidewire 10 is moved or translated toward a deflected position, the lever arm tends to remain in a generally straightened position until it contacts an inner surface of the tubular member 12 at a contact point 70, as seen in FIG. 2. In some embodiments, the contact point 70 may not be a single point and may include an edge, a surface, a plurality of points, and/or other feature(s), as may be seen below. In some cases, contact between the pressure sensor 20 and the inner surface of the tubular member 12 may mechanically deflect or translate the membrane 72, thereby causing a pressure shift or offset to be detected by the pressure sensor 20, undesirably resulting in an altered pressure reading. In some cases, the pressure shift or offset may be increased the more distally the contact point 70 is disposed along the head of the pressure sensor 20 (i.e., closer to the membrane 72 and/or the distal end of the head of the pressure sensor 20). In some cases, the greater the side stress applied at a distal end or edge of the pressure sensor 20, the greater the pressure shift or offset may be. As a result, the magnitude of the pressure shift or offset may be variable and difficult to compensate for when displaying the detected pressure. Preventing contact between a distalmost edge of the head and/or the membrane 72 of the pressure sensor 20 and the inner surface of the tubular member 12 may minimize or eliminate side stress induced pressure shifts or offsets, thereby enabling more correct and/or more precise pressure measurements, independent of the positioning of the tubular member 12 (i.e., whether the tubular member 12 is disposed in the generally straightened position or the deflected position).

For simplicity, the pressure sensor(s) described in this disclosure are illustrated as being generally cylindrical in shape. However, the skilled artisan will recognize that other shapes including round, spherical, square, cubical, rectangular, triangular, pentagonal, hexagonal, octagonal, or other suitable geometric and/or prismatic shapes with varying quantities of sides and/or edges are contemplated and may be used in accordance with the present disclosure.

Similarly, some or all elements of the guidewire 10, the tubular member 12, the proximal portion 14, the distal portion 16, the sleeve 17, the lumen 22, the fiber optic 24, the tip member 30, the shaping member 32, the spring or coil member 34, and/or other elements of the disclosure may take any suitable shape or combination of shapes, as appropriate. Illustratively, the elements may be shown as being generally round or cylindrical, but the skilled artisan will recognize that other shapes including spherical, square, cubical, rectangular, triangular, pentagonal, hexagonal, octagonal, or other suitable geometric and/or prismatic shapes with varying quantities of sides and/or edges are contemplated and may be used in accordance with the present disclosure.

Figure 3:
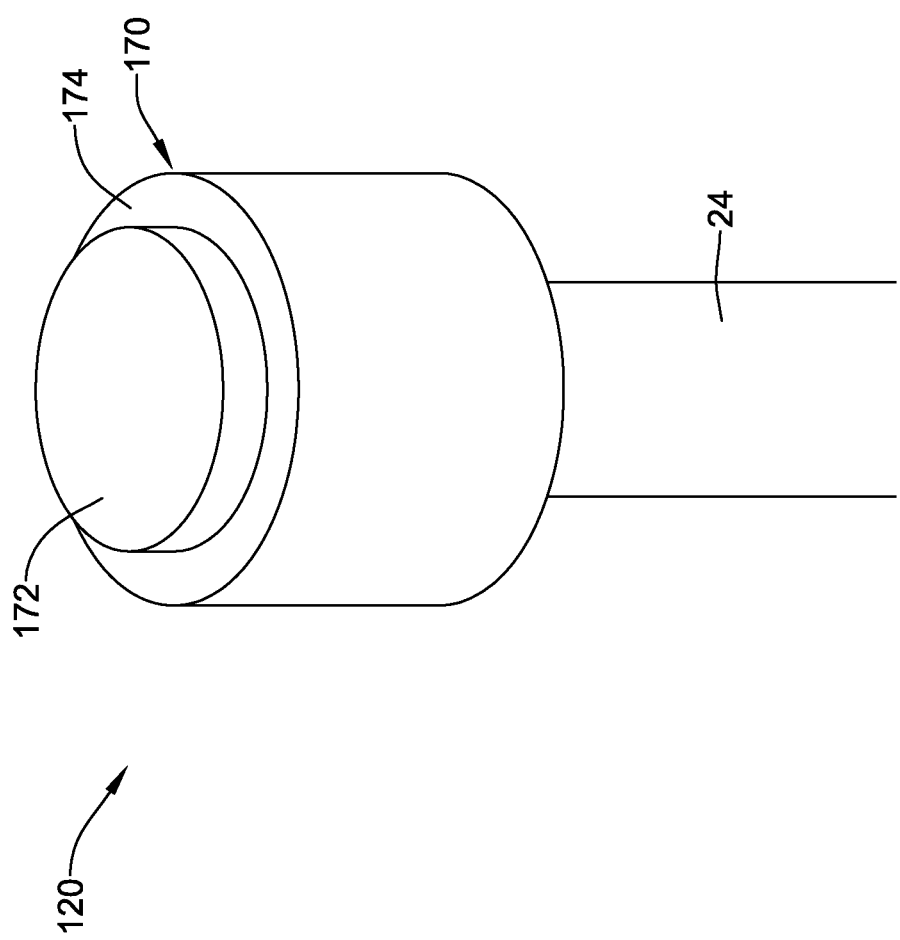
FIG. 3 is a partial perspective view of an example sensor head.

In some embodiments, a guidewire 10 may include a pressure sensor 120 having a head disposed at a distal end of a fiber optic 24, as illustrated in FIG. 3 for example. In some embodiments, the pressure sensor 120 may include a pressure-sensitive membrane 172 disposed on a distal end thereof. In some embodiments, the membrane 172 may extend across the distal end of the pressure sensor 120. In some embodiments, the membrane 172 may extend across a portion of the distal end of the pressure sensor 120. For example, in some embodiments, the membrane 172 may be substantially centered on the distal end of the pressure sensor 120, but may not extend or reach to or over an edge of the distal end of the pressure sensor 120. In some embodiments, the pressure sensor 120 may include a contact member 174 disposed about the head of the pressure sensor 120. In some embodiments, the contact member 174 may extend radially outward from the pressure sensor 120. In some embodiments, the contact member 174 may be radially spaced apart from an inner surface of the tubular member 12 when in the generally straightened position. In some embodiments, the contact member 174 may be capable of providing a contact point 170 between the contact member 174 and an inner surface of the tubular member 12 when in the deflected position. In some embodiments, the contact point 170 may be axially spaced apart from the distal end of the pressure sensor 120 and/or the membrane 172 along a longitudinal axis of the pressure sensor 120, thereby minimizing side stress at the distal end of the pressure sensor 120 and/or the membrane 172. In some embodiments, the contact point 170 may not be a single point and may include an edge, a surface, a plurality of points, and/or other feature(s). In some embodiments, the contact point 170 may be disposed proximally and/or radially outward of the distal end of the head of the pressure sensor 120 and/or the membrane 172.

Figure 3A:
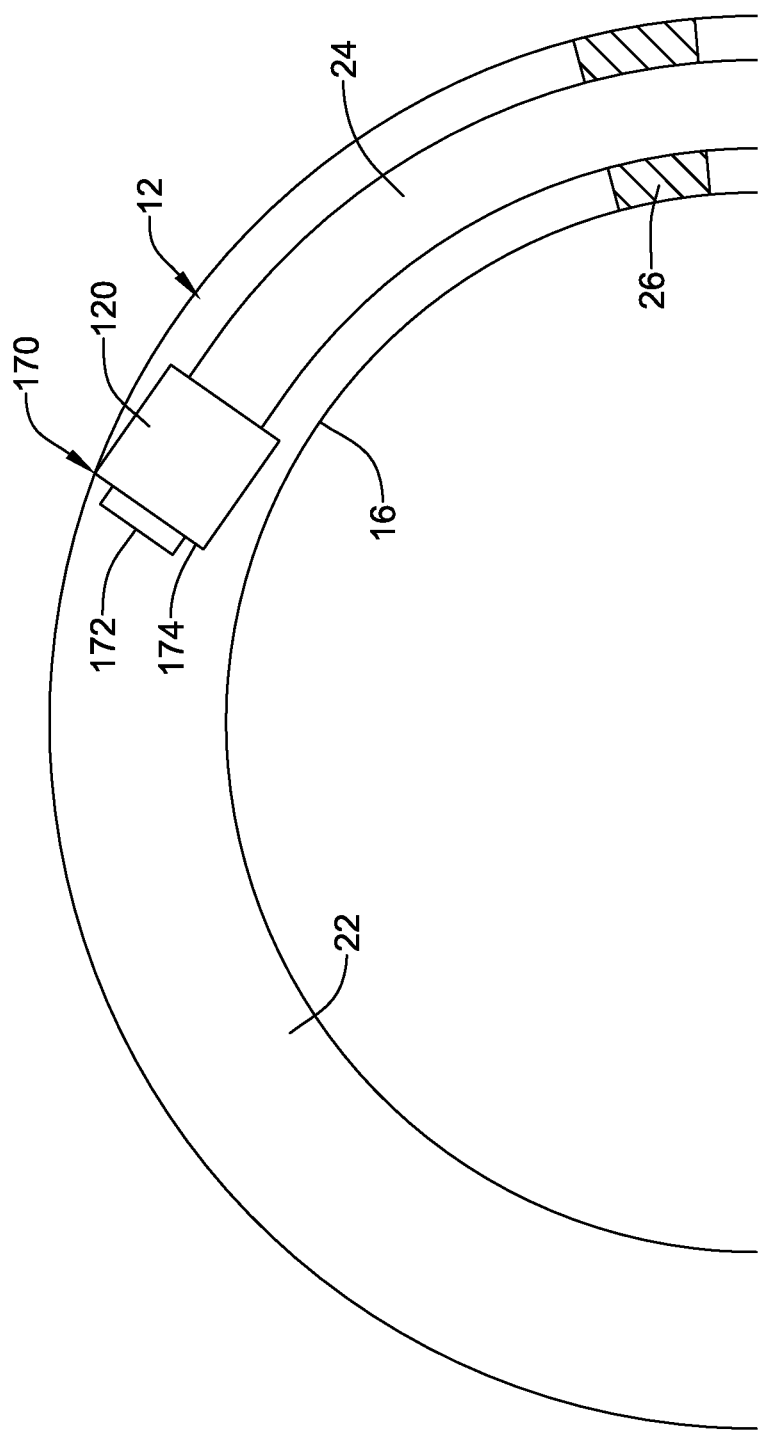
FIG. 3A is a partial cross-sectional side view of the example sensor head of FIG. 3 in a deflected medical device.

In some embodiments, the contact member 174 may be integrally formed with the head of the pressure sensor 120 from a single monolithic piece of material. In some embodiments, the contact member 174 may be separately formed from a similar material to the head of the pressure sensor 120 as a tubular sleeve or similar element, or the contact member 174 may be separately formed from a different material than the head of the pressure sensor 120 as a tubular sleeve or similar element. In some embodiments, the contact member 174 may be fixedly attached or joined to the head of the pressure sensor 120 by adhesive bonding, welding, soldering, friction fit, interference fit, threaded or mechanical fastening, or other suitable means. In some embodiments, the contact member 174 may form a step at, or immediately adjacent to, a distal end of the pressure sensor 120, wherein the distal end of the head and/or the membrane 172 may be disposed radially inward from the contact point 170. In use, the contact member 174 may be radially spaced apart from an inner surface of the tubular member 12 when in the generally straightened position. In some embodiments, a distal end of the pressure sensor 120 does not contact an inner surface of the tubular member 12 in the generally straightened position. In some embodiments, the contact point 170 may contact an inner surface of the tubular member 12 when the guidewire 10 is moved or translated toward or into a deflected position. As may be seen in FIG. 3A for example, the distal end of the head and/or the membrane 172 of the pressure sensor 120 may be spaced apart from the inner surface of the tubular member 12 by the contact member 174 in the deflected position, and/or the distal end of the pressure sensor 120 and/or the membrane 172 does not contact the inner surface of the tubular member 12 in the deflected position, thereby minimizing or eliminating side stress induced pressure shifts or offsets.

Figure 4A:
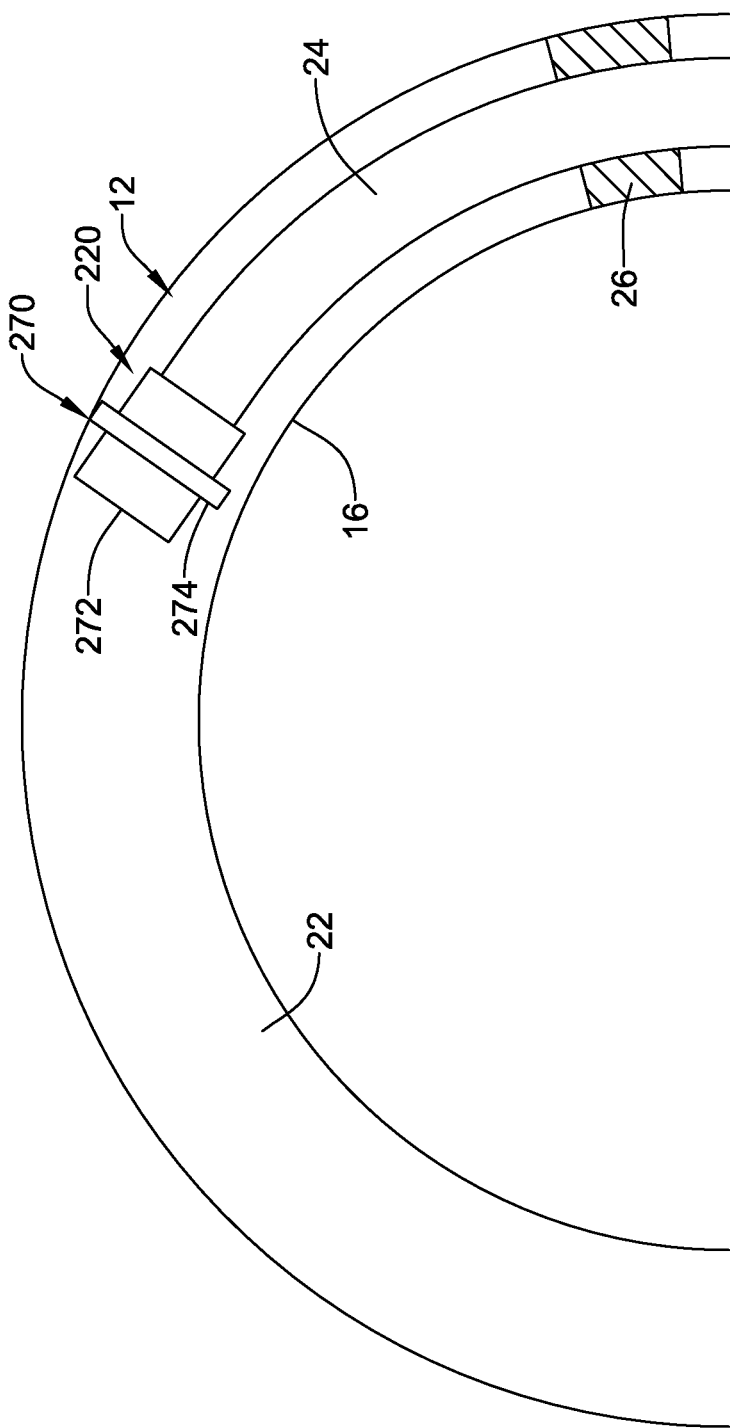
FIG. 4A is a partial cross-sectional side view of the example sensor head of FIG. 4 in a deflected medical device.

In some embodiments, a guidewire 10 may include a pressure sensor 220 having a head disposed at a distal end of a fiber optic 24, as illustrated in FIG. 4 for example. In some embodiments, the pressure sensor 220 may include a pressure-sensitive membrane 272 disposed on a distal end thereof. In some embodiments, the membrane 272 may extend across the distal end of the pressure sensor 220. In some embodiments, the membrane 272 may extend across a portion of the distal end of the pressure sensor 220. For example, in some embodiments, the membrane 272 may be substantially centered on the distal end of the pressure sensor 220, but may not extend or reach to or over an edge of the distal end of the pressure sensor 220. In some embodiments, the pressure sensor 220 may include a contact member 274 disposed about the head of the pressure sensor 220. In some embodiments, the contact member 274 may extend radially outward from the pressure sensor 220. In some embodiments, the contact member 274 may be radially spaced apart from an inner surface of the tubular member 12 when in the generally straightened position. In some embodiments, the contact member 274 may be capable of providing a contact point 270 between the contact member 274 and an inner surface of the tubular member 12 when in the deflected position. In some embodiments, the contact point 270 may be axially spaced apart from the distal end of the pressure sensor 220 and/or the membrane 272 along a longitudinal axis of the pressure sensor 220, thereby minimizing side stress at the distal end and/or the membrane 272. In some embodiments, the contact point 270 may not be a single point and may include an edge, a surface, a plurality of points, and/or other feature(s). In some embodiments, the contact point 270 may be disposed proximally and/or radially outward of the distal end of the head of the pressure sensor 220 and/or the membrane 272.

In some embodiments, the contact member 274 may be integrally formed with the head of the pressure sensor 220 from a single monolithic piece of material. In some embodiments, the contact member 274 may be separately formed from a similar material to the head of the pressure sensor 220 as a tubular sleeve, an annular ring, or a similar element, or the contact member 274 may be separately formed from a different material than the head of the pressure sensor 220 as a tubular sleeve, an annular ring, or a similar element. In some embodiments, the contact member 274 may be fixedly attached or joined to the head of the pressure sensor 220 by adhesive bonding, welding, soldering, friction fit, interference fit, threaded or mechanical fastening, or other suitable means. In some embodiments, the contact member 274 may form a step at, or immediately adjacent to, a distal end of the pressure sensor 220, wherein the distal end of the head and/or the membrane 272 may be disposed radially inward from the contact point 270. In use, the contact member 274 may be radially spaced apart from an inner surface of the tubular member 12 when in the generally straightened position. In some embodiments, a distal end of the pressure sensor 220 does not contact an inner surface of the tubular member 12 in the generally straightened position. In some embodiments, the contact point 270 may contact an inner surface of the tubular member 12 when the guidewire 10 is moved or translated toward or into a deflected position. As may be seen in FIG. 4A for example, the distal end of the head and/or the membrane 272 of the pressure sensor 220 may be spaced apart from the inner surface of the tubular member 12 by the contact member 274 in the deflected position, and/or the distal end of the pressure sensor 220 and/or the membrane 272 does not contact the inner surface of the tubular member 12 in the deflected position, thereby minimizing or eliminating side stress induced pressure shifts or offsets.

Figure 5A:
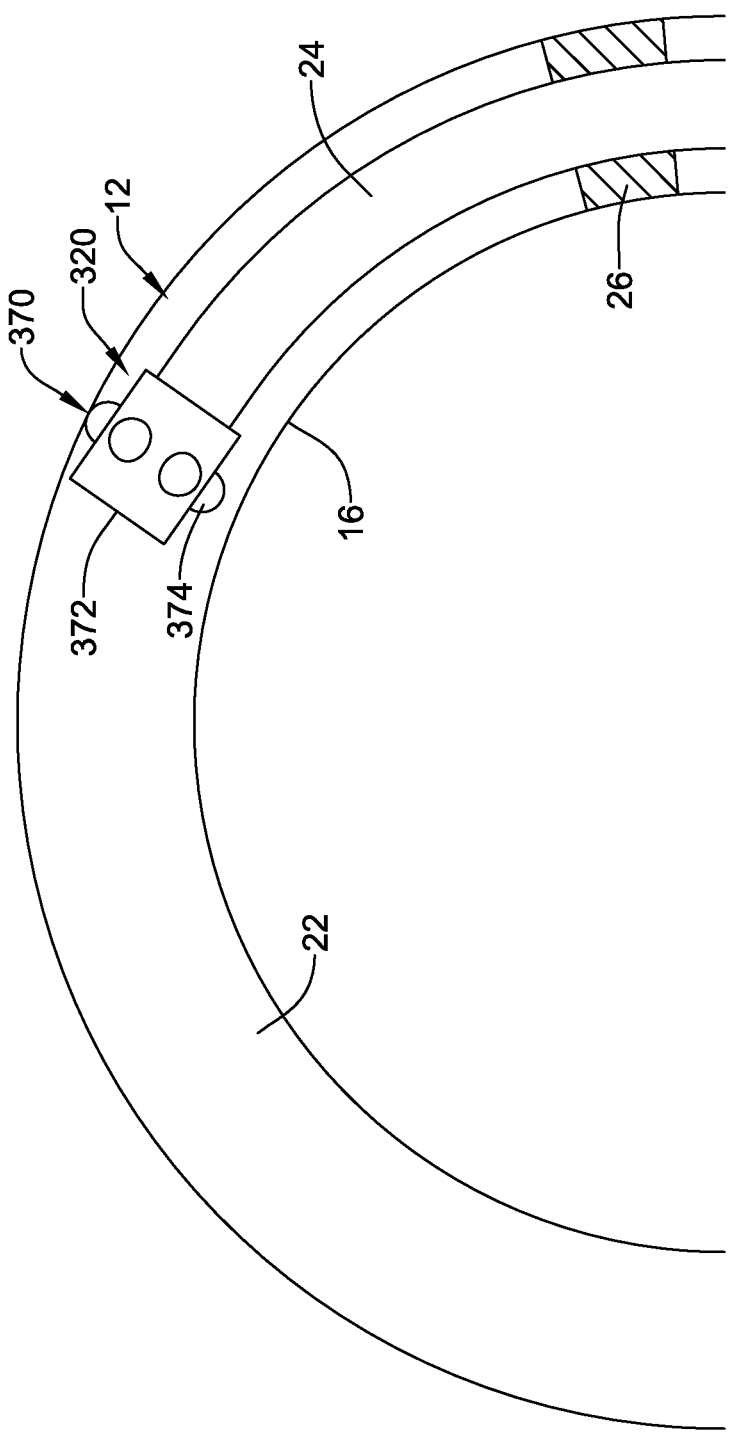
FIG. 5A is a partial cross-sectional side view of the example sensor head of FIG. 5 in a deflected medical device.

In some embodiments, a guidewire 10 may include a pressure sensor 320 having a head disposed at a distal end of a fiber optic 24, as illustrated in FIG. 5 for example. In some embodiments, the pressure sensor 320 may include a pressure-sensitive membrane 372 disposed on a distal end thereof. In some embodiments, the membrane 372 may extend across the distal end of the pressure sensor 320. In some embodiments, the membrane 372 may extend across a portion of the distal end of the pressure sensor 320. For example, in some embodiments, the membrane 372 may be substantially centered on the distal end of the pressure sensor 320, but may not extend or reach to or over an edge of the distal end of the pressure sensor 320. In some embodiments, the pressure sensor 320 may include one or more contact members 374 disposed on or about the head of the pressure sensor 320. In some embodiments, the one or more contact members 374 may include a plurality of contact members 374. In some embodiments, the one or more contact members 374 may extend radially outward from the pressure sensor 320. In some embodiments, the one or more contact members 374 may be radially spaced apart from an inner surface of the tubular member 12 when in the generally straightened position. In some embodiments, the one or more contact members 374 may be capable of providing a contact point 370 between the contact member 374 and an inner surface of the tubular member 12 when in the deflected position. In some embodiments, the contact point 370 may be axially spaced apart from the distal end of the pressure sensor 320 and/or the membrane 372 along a longitudinal axis of the pressure sensor 320, thereby minimizing side stress at the distal end and/or the membrane 372. In some embodiments, the contact point 370 may not be a single point and may include an edge, a surface, a plurality of points, and/or other feature(s). In some embodiments, the contact point 370 may be disposed proximally and/or radially outward of the distal end of the head of the pressure sensor 320 and/or the membrane 372.

In some embodiments, the one or more contact members 374 may be integrally formed with the head of the pressure sensor 320 from a single monolithic piece of material. In some embodiments, the one or more contact members 374 may be separately formed from a similar material to the head of the pressure sensor 320 as one or more protrusions, bumps, or similar elements, or the one or more contact members 374 may be separately formed from a different material than the head of the pressure sensor 320 as one or more protrusions, bumps, or similar elements. In some embodiments, the one or more contact members 374 may be fixedly attached or joined to the head of the pressure sensor 320 by adhesive bonding, welding, soldering, friction fit, interference fit, threaded or mechanical fastening, or other suitable means. In some embodiments, the one or more contact members 374 may form a plurality of protrusions extending radially outward from the pressure sensor 320, wherein the distal end of the head and/or the membrane 372 may be disposed radially inward from the contact point 370. In use, the one or more contact members 374 may be radially spaced apart from an inner surface of the tubular member 12 when in the generally straightened position. In some embodiments, a distal end of the pressure sensor 320 does not contact an inner surface of the tubular member 12 in the generally straightened position. In some embodiments, the contact point 370 may contact an inner surface of the tubular member 12 when the guidewire 10 is moved or translated toward or into a deflected position. As may be seen in FIG. 5A for example, the distal end of the head and/or the membrane 372 of the pressure sensor 320 may be spaced apart from the inner surface of the tubular member 12 by the one or more contact members 374 in the deflected position, and/or the distal end of the pressure sensor 320 and/or the membrane 372 does not contact the inner surface of the tubular member 12 in the deflected position, thereby minimizing or eliminating side stress induced pressure shifts or offsets.

Figure 6:
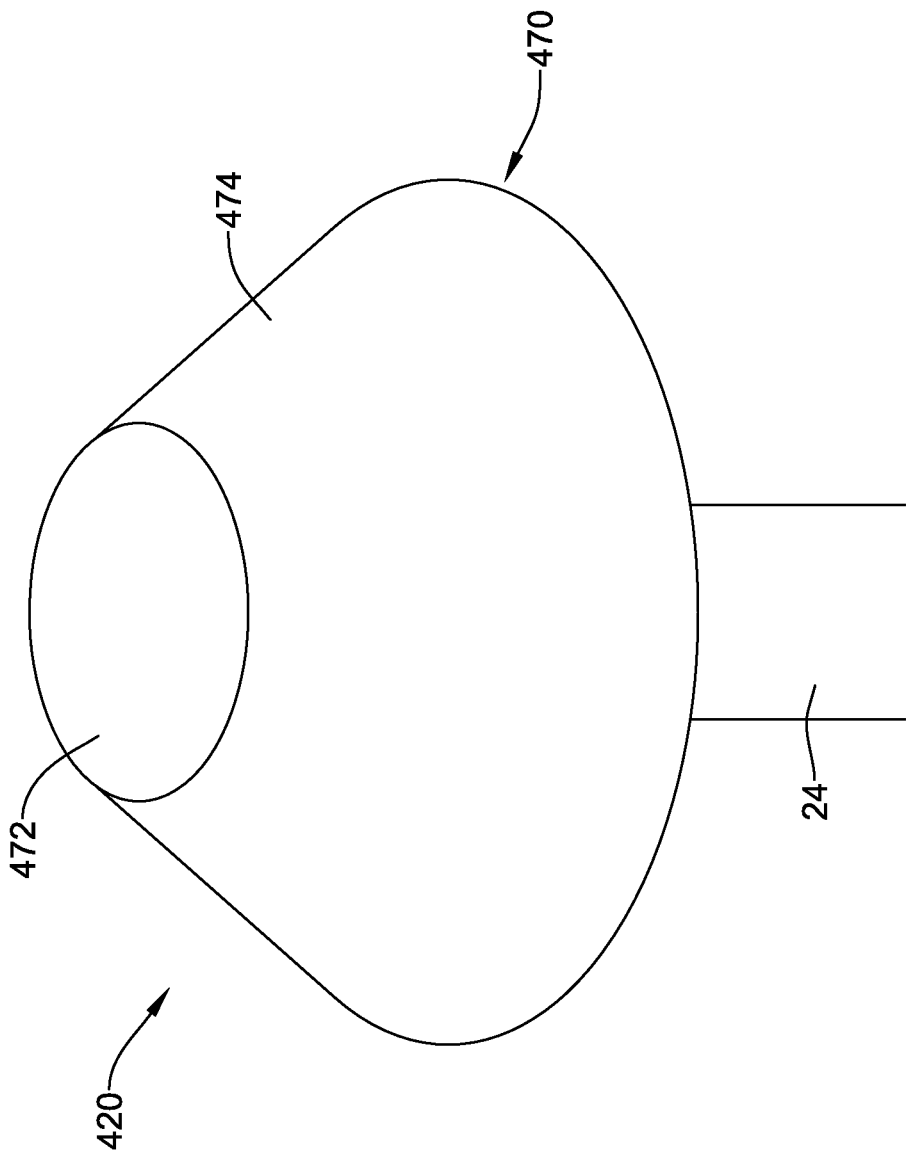
FIG. 6 is a partial perspective view of an example sensor head.

In some embodiments, a guidewire 10 may include a pressure sensor 420 having a head disposed at a distal end of a fiber optic 24, as illustrated in FIG. 6 for example. In some embodiments, the pressure sensor 420 may include a pressure-sensitive membrane 472 disposed on a distal end thereof. In some embodiments, the membrane 472 may extend across the distal end of the pressure sensor 420. In some embodiments, the membrane 472 may extend across a portion of the distal end of the pressure sensor 420. For example, in some embodiments, the membrane 472 may be substantially centered on the distal end of the pressure sensor 420, but may not extend or reach to or over an edge of the distal end of the pressure sensor 420. In some embodiments, the pressure sensor 420 may include a contact member 474 disposed about the head of the pressure sensor 420 or formed as a part of the head of the pressure sensor 420. In some embodiments, the contact member 474 may extend radially outward from the pressure sensor 420. In some embodiments, the contact member 474 may be radially spaced apart from an inner surface of the tubular member 12 when in the generally straightened position. In some embodiments, the contact member 474 may be capable of providing a contact point 470 between the contact member 474 and an inner surface of the tubular member 12 when in the deflected position. In some embodiments, the contact point 470 may be axially spaced apart from the distal end of the pressure sensor 420 and/or the membrane 472 along a longitudinal axis of the pressure sensor 420, thereby minimizing side stress at the distal end and/or the membrane 472. In some embodiments, the contact point 470 may not be a single point and may include an edge, a surface, a plurality of points, and/or other feature(s). In some embodiments, the contact point 470 may be disposed proximally and/or radially outward of the distal end of the head of the pressure sensor 420 and/or the membrane 472.

Figure 6A:
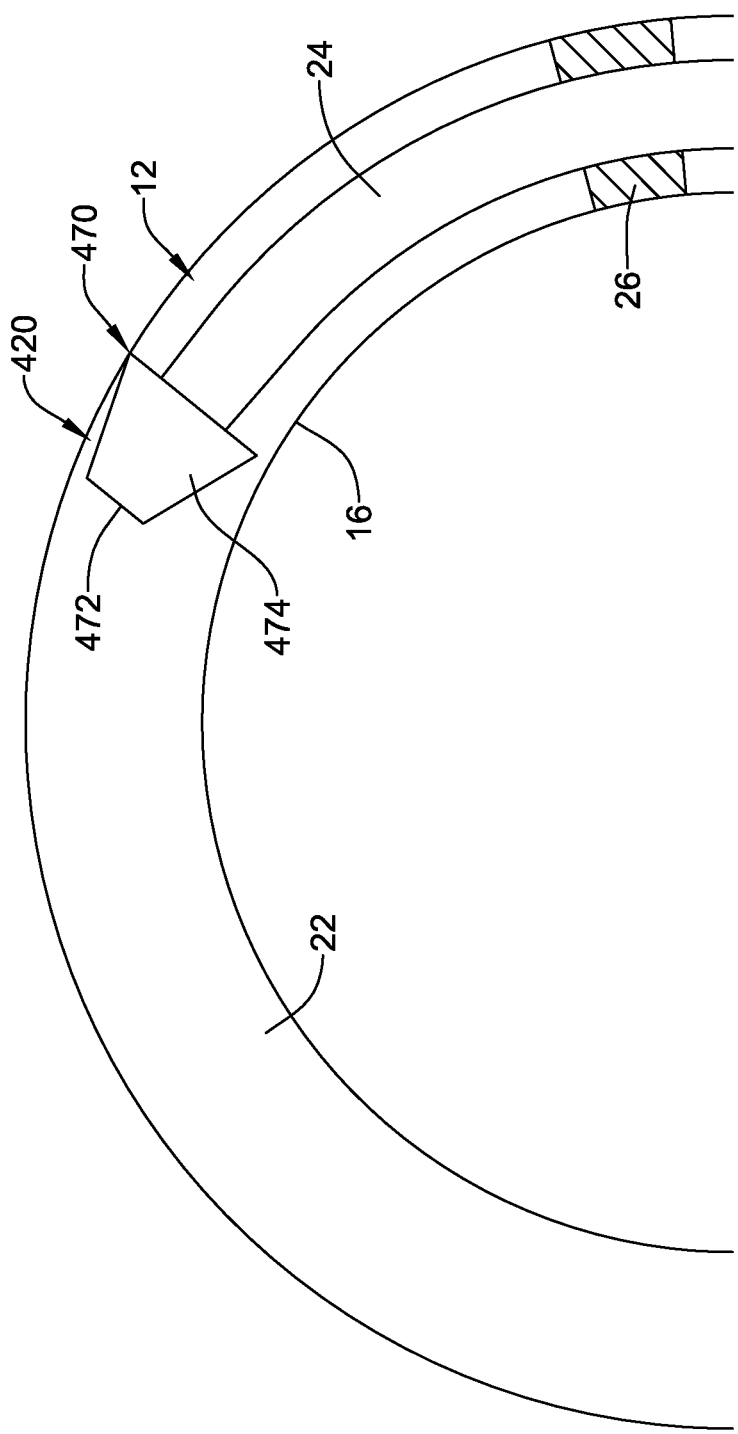
FIG. 6A is a partial cross-sectional side view of the example sensor head of FIG. 6 in a deflected medical device.

In some embodiments, the contact member 474 may be integrally formed with the head of the pressure sensor 420 from a single monolithic piece of material. In some embodiments, the contact member 474 may be separately formed from a similar material to the head of the pressure sensor 420 as a tubular sleeve or similar element, or the contact member 474 may be separately formed from a different material than the head of the pressure sensor 420 as a tubular sleeve or similar element. In some embodiments, the contact member 474 may be fixedly attached or joined to the head of the pressure sensor 420 by adhesive bonding, welding, soldering, friction fit, interference fit, threaded or mechanical fastening, or other suitable means. In some embodiments, the contact member 474 may form an inward taper from the contact point 470 distally toward a distal end of the pressure sensor 420, wherein the distal end of the head and/or the membrane 472 may be disposed radially inward from the contact point 470. In some embodiments, an outer surface of the contact member 474 may form an angle with or relative to a longitudinal axis of the sensor head 420. In some embodiments, the angle may be formed within a range of about 5 degrees to about 45 degrees, or the angle may be formed at about 5 degrees, about 10 degrees, about 15 degrees, about 20 degrees, about 25 degrees, about 30 degrees, about 35 degrees, about 40 degrees, about 45 degrees, or other suitable angle(s). In use, the contact member 474 may be radially spaced apart from an inner surface of the tubular member 12 when in the generally straightened position. In some embodiments, a distal end of the pressure sensor 420 does not contact an inner surface of the tubular member 12 in the generally straightened position. In some embodiments, the contact point 470 may contact an inner surface of the tubular member 12 when the guidewire 10 is moved or translated toward or into a deflected position. As may be seen in FIG. 6A for example, the distal end of the head and/or the membrane 472 of the pressure sensor 420 may be spaced apart from the inner surface of the tubular member 12 by the contact member 474 in the deflected position, and/or the distal end of the pressure sensor 420 and/or the membrane 472 does not contact the inner surface of the tubular member 12 in the deflected position, thereby minimizing or eliminating side stress induced pressure shifts or offsets.

Figure 7A:
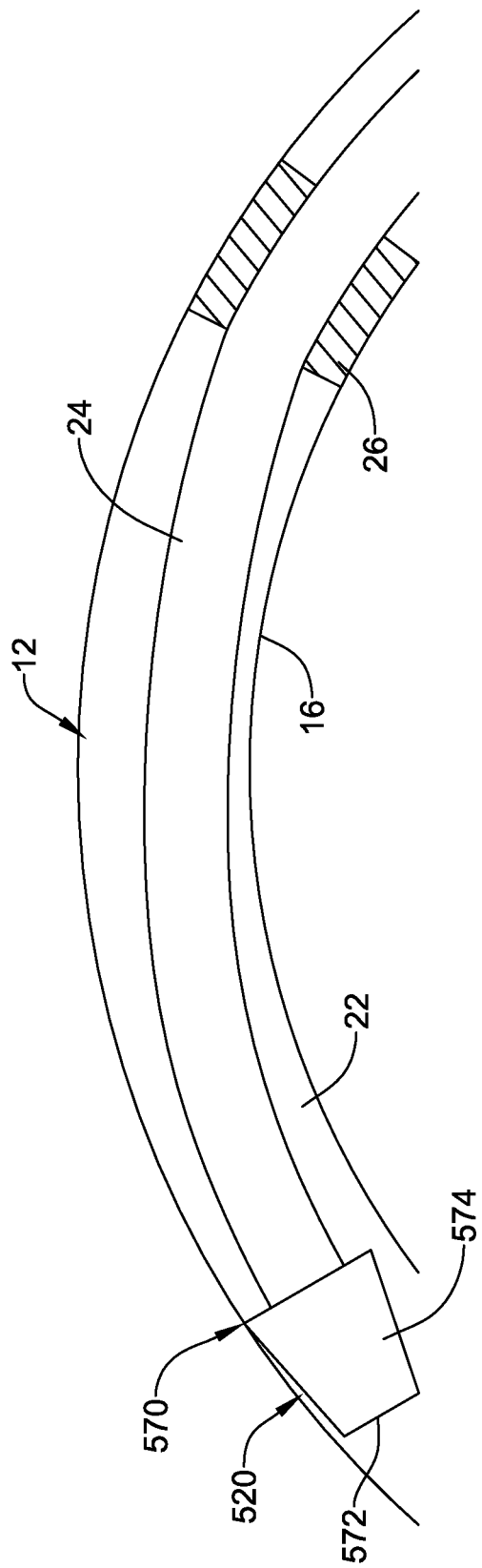
FIG. 7A is a partial cross-sectional side view of the example sensor head of FIG. 7 in a deflected medical device.

In some embodiments, a guidewire 10 may include a pressure sensor 520 having a head disposed at a distal end of a fiber optic 24, as illustrated in FIG. 7 for example. In some embodiments, the pressure sensor 520 may include a pressure-sensitive membrane 572 disposed on a distal end thereof. In some embodiments, the membrane 572 may extend across the distal end of the pressure sensor 520. In some embodiments, the membrane 572 may extend across a portion of the distal end of the pressure sensor 520. For example, in some embodiments, the membrane 572 may be substantially centered on the distal end of the pressure sensor 520, but may not extend or reach to or over an edge of the distal end of the pressure sensor 520. In some embodiments, the pressure sensor 520 may include a contact member 574 disposed about the head of the pressure sensor 520 or formed as a part of the head of the pressure sensor 520. In some embodiments, the contact member 574 may extend radially outward from the pressure sensor 520. In some embodiments, the contact member 574 may be radially spaced apart from an inner surface of the tubular member 12 when in the generally straightened position. In some embodiments, the contact member 574 may be capable of providing a contact point 570 between the contact member 574 and an inner surface of the tubular member 12 when in the deflected position. In some embodiments, the contact point 570 may be axially spaced apart from the distal end of the pressure sensor 520 and/or the membrane 572 along a longitudinal axis of the pressure sensor 520, thereby minimizing side stress at the distal end and/or the membrane 572. In some embodiments, the contact point 570 may not be a single point and may include an edge, a surface, a plurality of points, and/or other feature(s). In some embodiments, the contact point 570 may be disposed proximally and/or radially outward of the distal end of the head of the pressure sensor 520 and/or the membrane 572.

In some embodiments, the contact member 574 may be integrally formed with the head of the pressure sensor 520 from a single monolithic piece of material. In some embodiments, the contact member 574 may be separately formed from a similar material to the head of the pressure sensor 520 as a tubular sleeve or similar element, or the contact member 574 may be separately formed from a different material than the head of the pressure sensor 520 as a tubular sleeve or similar element. In some embodiments, the contact member 574 may be fixedly attached or joined to the head of the pressure sensor 520 by adhesive bonding, welding, soldering, friction fit, interference fit, threaded or mechanical fastening, or other suitable means. In some embodiments, the contact member 574 may form an inward taper from the contact point 570 distally toward a distal end of the pressure sensor 520, wherein the distal end of the head and/or the membrane 572 may be disposed radially inward from the contact point 570. In some embodiments, an outer surface of the contact member 574 may form an angle with or relative to a longitudinal axis of the sensor head 520. In some embodiments, the angle may be formed within a range of about 45 degrees to about 85 degrees, or the angle may be formed at about 45 degrees, about 50 degrees, about 55 degrees, about 60 degrees, about 65 degrees, about 70 degrees, about 75 degrees, about 80 degrees, about 85 degrees, or other suitable angle(s). In use, the contact member 574 may be radially spaced apart from an inner surface of the tubular member 12 when in the generally straightened position. In some embodiments, a distal end of the pressure sensor 520 does not contact an inner surface of the tubular member 12 in the generally straightened position. In some embodiments, the contact point 570 may contact an inner surface of the tubular member 12 when the guidewire 10 is moved or translated toward or into a deflected position. As may be seen in FIG. 7A for example, the distal end of the head and/or the membrane 572 of the pressure sensor 520 may be spaced apart from the inner surface of the tubular member 12 by the contact member 574 in the deflected position, and/or the distal end of the pressure sensor 520 and/or the membrane 572 does not contact the inner surface of the tubular member 12 in the deflected position, thereby minimizing or eliminating side stress induced pressure shifts or offsets.

In comparison, the pressure sensor 420 of FIG. 6 and the pressure sensor 520 of FIG. 7 may differ, for example, in the magnitude or angle of the taper formed by the outer surface of the contact member. In some embodiments, the pressure sensor 420 may include a contact member 474 having an outer surface formed at a greater angle relative to the longitudinal axis of the sensor head than the contact member 574 of the pressure sensor 520. In other words, the contact member 574 may have a shallower angle than the contact member 474, a more gradual taper than the contact member 474, and/or a contact point 570 that extends radially a shorter distance than the contact point 470 of the contact member 474. The configuration of the pressure sensor 420 permits the contact member 474 to function to protect the membrane 472 in a guidewire 10 having a short (or shorter) lever arm distance between the at least one attachment member 26 and the sensor head and/or the membrane 472. When the guidewire 10 is moved or translated into the deflected position, the tubular member 12 may form a bend radius. As the guidewire 10 is moved or translated toward the deflected position, the pressure sensor may remain in a substantially generally straightened position until contact is made between the pressure sensor and an inner surface of the tubular member 12. Then, the pressure sensor and the fiber optic 24 may bend along with the tubular member 12. The longer the lever arm, the sooner the pressure sensor may make contact with the inner surface of the tubular member 12 as the guidewire 10 is moved or translated toward the deflected position. As such, with a longer lever arm, contact may occur while the guidewire 10 forms a larger bend radius (and thus a shallower angle relative to a longitudinal axis thereof) than would be the case with a shorter lever arm. Accordingly, with a shorter lever arm, contact may occur while the guidewire 10 forms a tighter bend radius (and thus a sharper angle relative to a longitudinal axis thereof) compared to the longer lever arm. As noted above, contact at a distal end of the head of the pressure sensor (i.e., at or immediately adjacent to the membrane) may cause an undesirable shift or offset in the pressure measurement to occur.

Therefore, in some embodiments, the pressure sensor 420, which may include a contact member 474 having an outer surface formed at an angle relative to the longitudinal axis of the sensor head of greater than 45 degrees, may be suitable for use with a guidewire 10 configuration having a short lever arm and/or in locations where the guidewire 10 may encounter sharper bends and/or more tortuous vasculature. In some embodiments, the pressure sensor 520, which may include a contact member 574 having an outer surface formed at an angle relative to the longitudinal axis of the sensor head of less than 45 degrees, may be suitable for use with a guidewire 10 configuration having a long lever arm and/or in locations where the guidewire 10 may encounter gentler bends and/or less tortuous vasculature. However, other configurations and/or uses are contemplated, including embodiments where the pressure sensor 420 may be used with a long lever arm and embodiments where the pressure sensor 520 may be used with a short lever arm.

The materials that can be used for the various components of the guidewire 10 (and/or other guidewires disclosed herein), the various tubular members, and/or the contact members disclosed herein may include those commonly associated with medical devices. For simplicity purposes, the following discussion makes reference to the tubular member 12, the contact member(s), and other components of the guidewire 10. However, this is not intended to limit the devices and methods described herein, as the discussion may be applied to other similar tubular members and/or components of tubular members or devices disclosed herein.

The tubular member 12 and/or the contact member(s) may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the tubular member 12 and/or the contact member(s) may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the guidewire 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the guidewire 10 to achieve the same result.

In some embodiments, a degree of Magnetic Resonance Imaging (MRI) compatibility is imparted into the guidewire 10. For example, the tubular member 12 and/or the contact member(s), or portions thereof, may be made of a material that does not substantially distort the image and create substantial artifacts (i.e., gaps in the image). Certain ferromagnetic materials, for example, may not be suitable because they may create artifacts in an MRI image. The tubular member 12 and/or the contact member(s), or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

A sheath or covering (not shown) may be disposed over portions or all of the tubular member 12 that may define a generally smooth outer surface for the guidewire 10. In other embodiments, however, such a sheath or covering may be absent from a portion of all of the guidewire 10, such that the tubular member 12 may form the outer surface. The sheath and/or the contact member(s) may be made from a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, the exterior surface of the guidewire 10 (including, for example, the exterior surface of the tubular member 12 and/or the contact member(s)) may be sandblasted, beadblasted, sodium bicarbonate-blasted, electropolished, etc. In these as well as in some other embodiments, a coating, for example a lubricious, a hydrophilic, a protective, or other type of coating may be applied over portions or all of the sheath, or in embodiments without a sheath over portion(s) of the tubular member 12 and/or the contact member(s), or other portions of the guidewire 10. Alternatively, the sheath may comprise a lubricious, hydrophilic, protective, or other type of coating. Hydrophobic coatings such as fluoropolymers provide a dry lubricity which improves guidewire handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

The coating and/or sheath may be formed, for example, by coating, extrusion, co-extrusion, interrupted layer co-extrusion (ILC), or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

Various embodiments of arrangements and configurations of slots are also contemplated that may be used in addition to what is described above or may be used in alternate embodiments. For simplicity purposes, the following disclosure makes reference to the guidewire 10, the plurality of slots 18, and the tubular member 12. However, it can be appreciated that these variations may also be utilized for other slots and/or tubular members. In some embodiments, at least some, if not all of the plurality of slots 18 are disposed at the same or a similar angle with respect to the longitudinal axis of the tubular member 12. As shown, the plurality of slots 18 may be disposed at an angle that is perpendicular, or substantially perpendicular, and/or may be characterized as being disposed in a plane that is normal to the longitudinal axis of the tubular member 12. However, in other embodiments, the plurality of slots 18 may be disposed at an angle that is not perpendicular, and/or can be characterized as being disposed in a plane that is not normal to the longitudinal axis of the tubular member 12. Additionally, a group of one or more slots may be disposed at different angles relative to another group of one or more slots. The distribution and/or configuration of the plurality of slots 18 can also include, to the extent applicable, any of those disclosed in U.S. Pat. Publication No. US 2004/0181174, the entire disclosure of which is herein incorporated by reference.

The plurality of slots 18 may be provided to enhance the flexibility of the tubular member 12 while still allowing for suitable torque transmission characteristics. The plurality of slots 18 may be formed such that one or more rings and/or tube segments interconnected by one or more segments and/or beams that are formed in the tubular member 12, and such tube segments and beams may include portions of the tubular member 12 that remain after the plurality of slots 18 are formed in the body of the tubular member 12. Such an interconnected structure may act to maintain a relatively high degree of torsional stiffness, while maintaining a desired level of lateral flexibility. In some embodiments, some adjacent slots can be formed such that they include portions that overlap with each other about the circumference of the tubular member 12. In other embodiments, some adjacent slots can be disposed such that they do not necessarily overlap with each other, but are disposed in a pattern that provides the desired degree of lateral flexibility.

Additionally, the plurality of slots 18 may be arranged along the length of, or about the circumference of, the tubular member 12 to achieve desired properties. For example, adjacent slots, or groups of slots, can be arranged in a symmetrical pattern, such as being disposed essentially equally on opposite sides about the circumference of the tubular member 12, or can be rotated by an angle relative to each other about the axis of the tubular member 12. Additionally, adjacent slots, or groups of slots, may be equally spaced along the length of the tubular member 12, or can be arranged in an increasing or decreasing density pattern, or can be arranged in a non-symmetric or irregular pattern. Other characteristics, such as slot size, slot shape, and/or slot angle with respect to the longitudinal axis of the tubular member 12, may also be varied along the length of the tubular member 12 in order to vary the flexibility or other properties. In other embodiments, moreover, it is contemplated that portions of the tubular member 12, such as the proximal portion 14, the distal portion 16, or the entire tubular member 12, may not include any such slots.

As suggested herein, the plurality of slots 18 may be formed in groups of two, three, four, five, or more slots, which may be located at substantially the same location along the axis of the tubular member 12. Alternatively, a single slot may be disposed at some or all of these locations. Within the groups of slots, there may be included slots that are equal in size (i.e., span the same circumferential distance around the tubular member 12). In some of these as well as other embodiments, at least some slots in a group are unequal in size (i.e., span a different circumferential distance around tubular member 12). Longitudinally adjacent groups of slots may have the same or different configurations. For example, some embodiments of the tubular member 12 include slots that are equal in size in a first group and then unequally sized in an adjacent group. It may be appreciated that in groups that have two slots that are equal in size and are symmetrically disposed around the tube circumference, the centroid of the pair of beams (i.e., the portion of the tubular member 12 remaining after the slots are formed therein) is coincident with the central axis of the tubular member 12. Conversely, in groups that have two slots that are unequal in size and whose centroids are directly opposed on the tube circumference, the centroid of the pair of beams can be offset from the central axis of the tubular member 12. Some embodiments of the tubular member 12 include only slot groups with centroids that are coincident with the central axis of the tubular member 12, only slot groups with centroids that are offset from the central axis of the tubular member 12, or slot groups with centroids that are coincident with the central axis of the tubular member 12 in a first group and offset from the central axis of the tubular member 12 in another group. The amount of offset may vary depending on the depth (or length) of the slots and may include other suitable distances.

The plurality of slots 18 may be formed by methods such as micro-machining, saw-cutting (e.g., using a diamond grit embedded semiconductor dicing blade), electron discharge machining, grinding, milling, casting, molding, chemically etching or treating, or other known methods, and the like. In some such embodiments, the structure of the tubular member 12 is formed by cutting and/or removing portions of the tube to form the plurality of slots 18. Some example embodiments of appropriate micromachining methods and other cutting methods, and structures for tubular members including slots and medical devices including tubular members are disclosed in U.S. Pat. Publication Nos. 2003/0069522 and 2004/0181174-A2; and U.S. Pat. Nos. 6,766,720; and 6,579,246, the entire disclosures of which are herein incorporated by reference. Some example embodiments of etching processes are described in U.S. Pat. No. 5,106,455, the entire disclosure of which is herein incorporated by reference. It should be noted that the methods for manufacturing the guidewire 10 may include forming the plurality of slots 18 in the tubular member 12 using these or other manufacturing steps.

In at least some embodiments, the plurality of slots 18 may be formed in the tubular member 12 using a laser cutting process. The laser cutting process may include a suitable laser and/or laser cutting apparatus. For example, the laser cutting process may utilize a fiber laser. Utilizing processes like laser cutting may be desirable for a number of reasons. For example, laser cutting processes may allow the tubular member 12 to be cut into a number of different cutting patterns in a precisely controlled manner. This may include variations in the slot width, ring width, beam height and/or width, etc. Furthermore, changes to the cutting pattern can be made without the need to replace the cutting instrument (e.g., blade). This may also allow smaller tubes (e.g., having a smaller outer diameter) to be used to form the tubular member 12 without being limited by a minimum cutting blade size. Consequently, the tubular member 12 may be fabricated for use in neurological devices or other devices where a relatively small size may be desired.

Additional Embodiments

A pressure sensing medical device is disclosed. The pressure sensing medical device comprises:

a guidewire including an elongate tubular member having a lumen extending therethrough; and an optical pressure sensor attached at a distal end of a fiber optic extending longitudinally within the lumen, the pressure sensor being disposed within a distal portion of the tubular member;

wherein the pressure sensor further includes a contact member capable of providing a contact point between the contact member and an inner surface of the tubular member, the contact point being axially spaced apart from a distal end of the pressure sensor.

Alternatively or additionally to any of the embodiments above, including at least one attachment member fixedly attaching the fiber optic to the tubular member within the distal portion, the at least one attachment member being proximally spaced apart from the pressure sensor.

Alternatively or additionally to any of the embodiments above, wherein the contact member is spaced apart from the inner surface of the tubular member in a generally straightened position.

Alternatively or additionally to any of the embodiments above, wherein the contact member is disposed about the pressure sensor.

Alternatively or additionally to any of the embodiments above, wherein the contact member extends outward from the pressure sensor.

Alternatively or additionally to any of the embodiments above, wherein the contact member is integrally formed with the pressure sensor from a single monolithic piece of material.

Alternatively or additionally to any of the embodiments above, wherein the contact member is formed as a step adjacent the distal end of the pressure sensor.

Alternatively or additionally to any of the embodiments above, wherein the contact member is formed as one or more protrusions.

Alternatively or additionally to any of the embodiments above, wherein the contact member is formed as an inward taper from the contact point distally toward the distal end of the pressure sensor.

Alternatively or additionally to any of the embodiments above, wherein the inward taper forms an angle with a longitudinal axis of the pressure sensor of less than about 45 degrees.

Alternatively or additionally to any of the embodiments above, wherein the inward taper forms an angle with a longitudinal axis of the pressure sensor of more than about 45 degrees.

Alternatively or additionally to any of the embodiments above, wherein the contact member is separately formed from the pressure sensor and subsequently fixedly attached thereto.

Alternatively or additionally to any of the embodiments above, wherein the contact member is formed as a tubular sleeve.

Alternatively or additionally to any of the embodiments above, wherein the contact member is formed as an annular ring.

Alternatively or additionally to any of the embodiments above, wherein the contact member is formed as one or more protrusions.

A pressure sensing medical device is disclosed. The pressure sensing medical device comprises:

a guidewire including an elongate tubular member having a lumen extending therethrough, the tubular member being movable between a generally straightened position and a deflected position; and an optical pressure sensor attached at a distal end of a fiber optic extending longitudinally within the lumen, the pressure sensor being disposed within a distal portion of the tubular member;

wherein the pressure sensor includes a pressure-sensitive membrane disposed on a distal end thereof;

wherein the pressure sensor further includes one or more contact members capable of providing a contact point between the contact member and an inner surface of the tubular member when in the deflected position, the contact point being axially spaced apart from the membrane along a longitudinal axis of the pressure sensor.

Alternatively or additionally to any of the embodiments above, including at least one attachment member attaching the fiber optic to the tubular member within the distal portion, the at least one attachment member being proximally spaced apart from the pressure sensor.

Alternatively or additionally to any of the embodiments above, wherein the one or more contact members is spaced apart from the inner surface of the tubular member when in the generally straightened position.

Alternatively or additionally to any of the embodiments above, wherein the one or more contact members is disposed about the pressure sensor.

Alternatively or additionally to any of the embodiments above, wherein the one or more contact members extends outward from the pressure sensor.

Alternatively or additionally to any of the embodiments above, wherein the one or more contact members is integrally formed with the pressure sensor from a single monolithic piece of material.

Alternatively or additionally to any of the embodiments above, wherein the one or more contact members is formed as a step adjacent the distal end of the pressure sensor.

Alternatively or additionally to any of the embodiments above, wherein the one or more contact members is formed as a plurality of protrusions.

Alternatively or additionally to any of the embodiments above, wherein the one or more contact members is formed as an inward taper from the contact point distally toward the distal end of the pressure sensor.

Alternatively or additionally to any of the embodiments above, wherein the inward taper forms an angle with a longitudinal axis of the pressure sensor of less than about 45 degrees.

Alternatively or additionally to any of the embodiments above, wherein the inward taper forms an angle with a longitudinal axis of the pressure sensor of more than about 45 degrees.

Alternatively or additionally to any of the embodiments above, wherein the one or more contact members is separately formed from the pressure sensor and subsequently fixedly attached thereto.

Alternatively or additionally to any of the embodiments above, wherein the one or more contact members is formed as a tubular sleeve.

Alternatively or additionally to any of the embodiments above, wherein the one or more contact members is formed as an annular ring.

Alternatively or additionally to any of the embodiments above, wherein the one or more contact members is formed as a plurality of protrusions.

A pressure sensing medical device is disclosed. The pressure sensing medical device comprises:

a guidewire including an elongate tubular member having a lumen extending therethrough, the tubular member being movable between a generally straightened position and a deflected position; and an optical pressure sensor attached at a distal end of a fiber optic extending longitudinally within the lumen, the pressure sensor being disposed within a distal portion of the tubular member;

wherein the pressure sensor includes a pressure-sensitive membrane disposed on a distal end thereof;

wherein the pressure sensor further includes one or more contact members capable of providing a contact point between the contact member and an inner surface of the tubular member when in the deflected position such that the membrane is spaced apart from the inner surface, the contact point being axially spaced apart from the membrane along a longitudinal axis of the pressure sensor.

Alternatively or additionally to any of the embodiments above, wherein the distal end of the pressure sensor does not contact the inner surface of the tubular member in the generally straightened position.

Alternatively or additionally to any of the embodiments above, wherein the distal end of the pressure sensor does not contact the inner surface of the tubular member in the deflected position.

Alternatively or additionally to any of the embodiments above, including at least one attachment member fixedly attaching the fiber optic to the tubular member within the distal portion, the at least one attachment member being proximally spaced apart from the pressure sensor.

Alternatively or additionally to any of the embodiments above, wherein the one or more contact members is disposed about the pressure sensor.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A pressure sensing medical device, comprising:
   a guidewire including an elongate tubular member having a lumen extending therethrough; and
   an optical pressure sensor attached at a distal end of a fiber optic extending longitudinally within the lumen, the pressure sensor being disposed within a distal portion of the tubular member;
   wherein the pressure sensor includes a sensor head having an outer surface, a distal end, and a proximal end disposed adjacent to the distal end of the fiber optic;
   wherein the pressure sensor further includes a contact member attached to the outer surface of the sensor head at a position between the proximal end and the distal end of the sensor head, the contact member being capable of providing one or more distinct contact points between the contact member and an inner surface of the tubular member, the one or more distinct contact points being axially spaced apart from a distal end of the pressure sensor.

2. The pressure sensing medical device of claim 1, including at least one attachment member fixedly attaching the fiber optic to the tubular member within the distal portion, the at least one attachment member being proximally spaced apart from the pressure sensor.

3. The pressure sensing medical device of claim 1, wherein the contact member is spaced apart from the inner surface of the tubular member in a generally straightened position.

4. The pressure sensing medical device of claim 1, wherein the contact member is disposed about the sensor head.

5. The pressure sensing medical device of claim 1, wherein the contact member extends outward from the sensor head.

6. The pressure sensing medical device of claim 1, wherein the contact member is integrally formed with the sensor head from a single monolithic piece of material.

7. The pressure sensing medical device of claim 6, wherein the contact member is formed as a step adjacent the distal end of the pressure sensor.

8. The pressure sensing medical device of claim 6, wherein the contact member is formed as one or more protrusions.

9. The pressure sensing medical device of claim 6, wherein the contact member is formed as an inward taper from the contact point distally toward the distal end of the pressure sensor.

10. The pressure sensing medical device of claim 9, wherein the inward taper forms an angle with a longitudinal axis of the pressure sensor of less than about 45 degrees.

11. The pressure sensing medical device of claim 9, wherein the inward taper forms an angle with a longitudinal axis of the pressure sensor of more than about 45 degrees.

12. The pressure sensing medical device of claim 1, wherein the contact member is separately formed from the pressure sensor and subsequently fixedly attached thereto.

13. The pressure sensing medical device of claim 12, wherein the contact member is formed as a tubular sleeve.

14. The pressure sensing medical device of claim 12, wherein the contact member is formed as an annular ring.

15. The pressure sensing medical device of claim 12, wherein the contact member is formed as one or more protrusions.

16. A pressure sensing medical device, comprising:

a guidewire including an elongate tubular member having a lumen extending therethrough, the tubular member being movable between a generally straightened position and a deflected position; and an optical pressure sensor attached at a distal end of a fiber optic extending longitudinally within the lumen, the pressure sensor being disposed within a distal portion of the tubular member;

wherein the optical pressure sensor includes a sensor head having and a deflectable membrane coupled to a distal end region of the sensor head;

wherein the sensor head has a proximal end disposed adjacent to the distal end of the fiber optic;

wherein the pressure sensor further includes one or more contact members coupled to an outer surface of the sensor head at a position between the distal end region and the proximal end of the sensor head, the one or more contact members being capable of providing one or more distinct contact points between the one or more contact members and an inner surface of the tubular member when in the deflected position, the one or more distinct contact points being axially spaced apart from the membrane along a longitudinal axis of the pressure sensor.

17. The pressure sensing medical device of claim 16, wherein the one or more contact members extends outward from the pressure sensor.

18. The pressure sensing medical device of claim 16, wherein the one or more contact members is integrally formed with the pressure sensor from a single monolithic piece of material.

19. The pressure sensing medical device of claim 18, wherein the one or more contact members is formed as an inward taper from the contact point distally toward the distal end of the pressure sensor.

20. A pressure sensing medical device, comprising:

a guidewire including an elongate tubular member having a lumen extending therethrough, the tubular member being movable between a generally straightened position and a deflected position; and an optical pressure sensor attached at a distal end of a fiber optic extending longitudinally within the lumen, the pressure sensor being disposed within a distal portion of the tubular member;

wherein the pressure sensor includes a sensor head and a pressure-sensitive membrane disposed on a distal end of the sensor head;

wherein the sensor head has a proximal end disposed adjacent to the distal end of the fiber optic;

wherein the pressure sensor further includes one or more contact members secured to an exterior surface of the sensor head at a position between the distal end and the proximal end of the sensor head, the one or more contact members being capable of providing one or more distinct contact points between the one or more contact members and an inner surface of the tubular member when in the deflected position such that the membrane is spaced apart from the inner surface, the one or more distinct contact points being axially spaced apart from the membrane along a longitudinal axis of the pressure sensor.

* * * * *